United States Patent [19]

Pelosi, Jr.

[11] 4,002,622
[45] Jan. 11, 1977

[54] 2-(3-CHLOROANILINO)-4H-3,1-BENZO-THIAZINE

[75] Inventor: Stanford Salvatore Pelosi, Jr., Norwich, N.Y.

[73] Assignee: Morton-Norwich Products, Inc., Norwich, N.Y.

[22] Filed: Oct. 30, 1975

[21] Appl. No.: 627,226

[52] U.S. Cl. .......................... 260/243 R; 424/246
[51] Int. Cl.² ...................................... C07D 279/08
[58] Field of Search ............................ 260/243 R

[56] References Cited
UNITED STATES PATENTS 3,417,085  12/1968  Kuch et al. .................. 260/243

*Primary Examiner*—John M. Ford
*Attorney, Agent, or Firm*—Anthony J. Franze

[57] ABSTRACT

2(3-Chloroanilino)-4H-3,1-benzothiazine is an effective anthelmintic agent.

1 Claim, No Drawings

2-(3-CHLOROANILINO)-4H-3,1-BENZOTHIAZINE

This invention relates to the compound 2-(3-chloroanilino)-4H-3,1-benzothiazine of the formula:

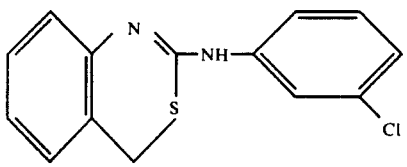

and a method for its preparation.

The compound of this invention is distinguished by its ability to combat helminth infection. When administered by gavage as a suspension in aqueous solution to mice harboring *Syphacia obvelata* or *Nippostrongylus brasiliensis* worms, this compound accomplished an 83 and 47% reduction of the worm burden at a dose of 100 and 300 mg/kg, respectively. The compound of this invention can be combined in obvious forms such as suspensions and dispersions to provide conveniently administered dosage compositions.

The compound of this invention is readily prepared. Currently it is preferred to react 3-chloroaniline with 2-methylthio-4H-3,1-benzothiazine. In order that this invention may be fully available to and understood by those skilled in the art, the method now preferred is briefly described.

2-(3-Chloroanilino)-4H-3,1-benzothiazine

A mixture of 2-methylthio-4H-3,1-benzothiazine (57 g, 0.29 mole) and 3-chloroaniline (37 g, 0.29 mole) in n-butanol (250 ml) was refluxed overnight. After cooling in ice, the solid was collected by filtration and recrystallized from ethanol-water mixture to give 36 g (45%) of product, m.p. 183°–184°.

Anal. Calcd. for $C_{14}H_{11}ClN_2S$: C, 61.19; H, 4.03; N, 10.19.

Found: C, 60.95; H, 4.15, N, 10.10.

What is claimed is:

1. The compound 2-(3-chloroanilino)-4H-3,1-benzothiazine of the formula:

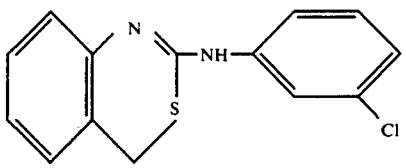

* * * * *